US011571496B2

(12) United States Patent
Moss et al.

(10) Patent No.: US 11,571,496 B2
(45) Date of Patent: Feb. 7, 2023

(54) SYSTEM AND METHOD FOR FABRICATING A CORNEA

(71) Applicant: Advanced Solutions Life Sciences, LLC, Louisville, KY (US)

(72) Inventors: Sarah Moss, Louisville, KY (US); James Hoying, Louisville, KY (US); Hannah Strobel, Louisville, KY (US)

(73) Assignee: Advanced Solutions Life Sciences, LLC, Louisville, KY (US)

(*) Notice: Subject to any disclaimer, the term of this patent is extended or adjusted under 35 U.S.C. 154(b) by 185 days.

(21) Appl. No.: 16/891,153

(22) Filed: Jun. 3, 2020

(65) Prior Publication Data
US 2020/0376165 A1 Dec. 3, 2020

Related U.S. Application Data

(60) Provisional application No. 62/856,380, filed on Jun. 3, 2019.

(51) Int. Cl.
A61L 27/38 (2006.01)
A61F 2/14 (2006.01)
(Continued)

(52) U.S. Cl.
CPC .......... A61L 27/3808 (2013.01); A61F 2/142 (2013.01); A61L 27/222 (2013.01);
(Continued)

(58) Field of Classification Search
CPC ............... A61L 27/3808; A61L 27/222; A61L 27/3813; A61L 27/24; A61L 27/56;
(Continued)

(56) References Cited

U.S. PATENT DOCUMENTS 4,969,912 A 11/1990 Kelman et al.
5,108,428 A 4/1992 Capecchi et al.
(Continued)

FOREIGN PATENT DOCUMENTS

CN 105331539 A 2/2016
JP 2014030596 A 2/2014
(Continued)

OTHER PUBLICATIONS

International Search Report and Written Opinon of the International Searching Authority, dated Aug. 31, 2020, PCT.

Primary Examiner — Michael L Hobbs
(74) Attorney, Agent, or Firm — Dinsmore & Shohl LLP

(57) ABSTRACT

A method for fabricating a cornea includes affixing a frame to at least one cell culture insert comprising a generally cylindrical structure having a proximal end and a distal end, a base disposed at the proximal end, and a porous membrane disposed between the proximal end and the distal end; affixing a dome-shaped member to the porous membrane within the frame, the dome-shaped member comprising a crown, a dome base, and a surface connecting the crown and the dome base; depositing a material comprising a matrix-forming compound on the frame such that the crown and at least a portion of the surface of the dome-shaped member is coated with the material comprising the matrix-forming compound; and removing the dome-shaped member to produce a fabricated cornea attached to the frame. A system for fabricating a cornea and a cornea scaffold are also described herein.

8 Claims, 10 Drawing Sheets

(51) Int. Cl.
*C12M 1/12* (2006.01)
*A61L 27/22* (2006.01)
*C12M 1/00* (2006.01)
*A61F 2/00* (2006.01)

(52) U.S. Cl.
CPC ............ *C12M 23/06* (2013.01); *C12M 25/14* (2013.01); *C12M 29/10* (2013.01); *A61F 2002/0081* (2013.01); *A61F 2230/0013* (2013.01); *A61F 2240/002* (2013.01); *A61L 2430/16* (2013.01)

(58) Field of Classification Search
CPC ......... A61L 2430/16; A61F 2/142; A61F 2002/0081; A61F 2230/0013; A61F 2240/002; A61F 2240/001; C12M 23/06; C12M 25/14; C12M 29/10
See application file for complete search history.

(56) References Cited

U.S. PATENT DOCUMENTS

| | | |
|---|---|---|
| 5,458,819 A | 10/1995 | Chirila et al. |
| 5,657,506 A | 8/1997 | Pankow |
| 5,916,494 A | 6/1999 | Widman et al. |
| 2010/0112690 A1* | 5/2010 | Eddington ............ C12M 29/10 435/297.5 |
| 2015/0024495 A1* | 1/2015 | Morgan ................ C12M 29/10 435/286.2 |
| 2016/0144069 A1 | 5/2016 | Cho et al. |
| 2017/0229043 A1* | 8/2017 | Huh ....................... G09B 23/32 |

FOREIGN PATENT DOCUMENTS

| | | | | |
|---|---|---|---|---|
| WO | WO-03077794 A2 * | 9/2003 | ........... | A61F 9/0017 |
| WO | WO-2012045368 A1 * | 4/2012 | ............. | A61P 25/28 |
| WO | 2014104366 A1 | 7/2014 | | |

\* cited by examiner

SYSTEM AND METHOD FOR FABRICATING A CORNEA

CROSS-REFERENCE TO RELATED APPLICATIONS

The present disclosure claims the benefit of U.S. Provisional App. No. 62/856,380, filed Jun. 3, 2019, entitled "SYSTEM AND METHOD FOR FABRICATING A LIVING CORNEA," the entirety of which is incorporated by reference herein.

TECHNICAL FIELD

The present disclosure relates to cornea fabrication, more particularly, to use of a manipulatable system to fabricate a living cornea.

BACKGROUND

The cornea is the clear, curved tissue at the front of the eye that protects the eye interior while allowing light to pass through from the exterior of the eye to the visual processing structures and systems inside the eye and nervous system. Corneal replacement therapy is used to restore vision to a person with a damaged cornea from conditions including keratoconus, Fuchs' dystrophy, thinning cornea, cornea scarring, clouding of the cornea, swelling of the cornea, corneal ulcers, and complications caused by eye surgery. In addition to corneal replacement therapy, a supply of corneas is also needed to conduct research to address these and other conditions. Currently, corneal replacement and associated scientific research require tissue donation from a cadaverous donor. A need therefore exists for artificial techniques to efficiently fabricate corneas for corneal replacement therapy and as a supply of samples for corneal research.

BRIEF SUMMARY

In an embodiment, a method for fabricating a cornea includes affixing a frame to at least one cell culture insert comprising a generally cylindrical structure having a proximal end and a distal end, a base disposed at the proximal end, and a porous membrane disposed between the proximal end and the distal end; affixing a dome-shaped member to the porous membrane within the frame, the dome-shaped member comprising a crown, a dome base, and a surface connecting the crown and the dome base; depositing a material comprising a matrix-forming compound on the frame such that the crown and at least a portion of the surface of the dome-shaped member is coated with the material comprising the matrix-forming compound; and removing the dome-shaped member to produce a fabricated cornea attached to the frame.

In another embodiment, a system for fabricating a cornea includes at least one cell culture insert, the cell culture insert comprising a generally cylindrical structure having a proximal end and a distal end, a base disposed at the proximal end, and a porous membrane disposed between the proximal end and the distal end; and a frame disposed on the at least one cell culture insert.

In yet another embodiment, a fabricated cornea scaffold includes a non-naturally occurring domed structure having a convex surface and a concave surface, the non-naturally occurring domed structure comprising a matrix comprising at least one matrix-forming compound.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
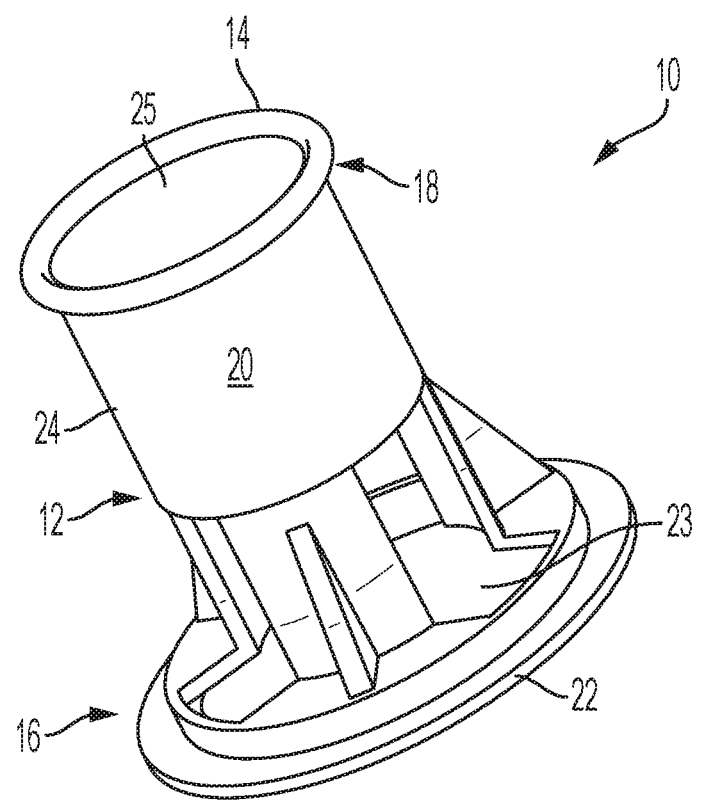
FIG. 1 illustrates a system for fabricating corneas, according to one or more embodiments shown and described herein.

Referring generally to the figures, embodiments of the present disclosure are directed to systems and methods for fabricating corneas. The systems and methods for fabricating corneas as described herein will allow for supply of corneas for replacement and research. The systems and methods described herein facilitate further processing of the fabricated corneas by providing a location for manipulating the corneas without contacting the corneas during fabrication and culturing.

Reference will now be made in detail to embodiments of the fabrication systems, and examples of such systems are illustrated in the accompanying drawings. Wherever possible, the same reference numerals will be used throughout the drawings to refer to the same or like parts. Various embodiments of the fabrication systems will be described in further detail herein with specific reference to the appended drawings.

Referring initially to FIG. 1, a system 10 for fabricating a cornea includes at least one cell culture insert 12 and a frame 14 disposed on the at least one cell culture insert 12. An exemplary cell culture insert 12 is commercially available as a TRANSWELL® Permeable Support. The cell culture insert 12 may be hollow and generally cylindrical in shape, with a proximal end 16 separated from a distal end 18 by cylindrical outer surface 20. Base 22 may be disposed at the proximal end 16 of the cell culture insert 12 and may include an aperture 23 allowing access to the hollow interior of the cylinder 24. A porous membrane 25 may be disposed between the proximal end 16 and the distal end 18. In embodiments, the porous membrane 25 may be closer to the distal end 18 of the cell culture insert 12 than to the proximal end 16.

Figure 2:
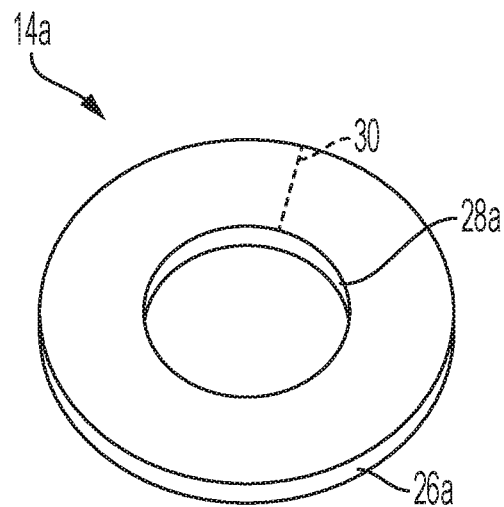
FIG. 2 illustrates a solid component of a frame used in a system for fabricating corneas, according to one or more embodiments shown and described herein.
Figure 3:
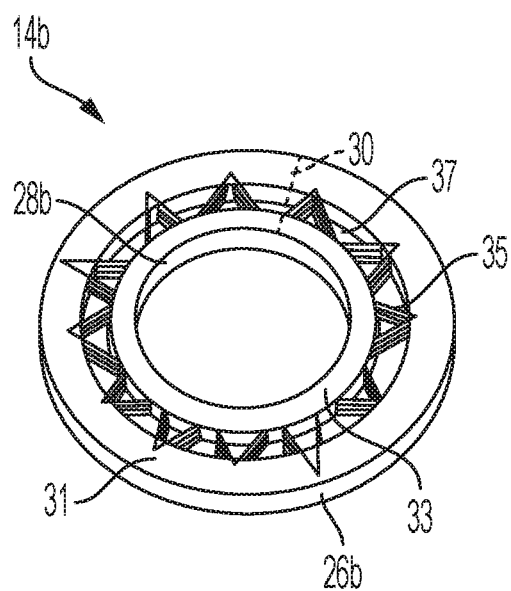
FIG. 3 illustrates a porous component of a frame used in a system for fabricating corneas, according to one or more embodiments shown and described herein.

Referring to FIGS. 2 and 3, frame 14 may be used to attach the cornea to cell culture insert 12 during fabrication of the cornea. Frame 14 may be unitary in structure but also may be composed of both a solid component 14a and a porous component 14b adjacent the solid component 14a. Both the solid component 14a and the porous component 14b are generally toroidal, or annular, in shape. Toroidal, or annular, shapes may be characterized in terms of an inner radius and an outer radius. Thus, solid component 14a and porous component 14b include an outer surface 26a, 26b, respectively, at the outer limit of the outer radius, and an inner surface 28a, 28b, respectively, at the inner limit of the inner radius, separated by a thickness 30. The porous component 14b includes an outer ring 31 and an inner ring 33 separated by framework structures 35, the interstices of which form pores 37. In embodiments, inner surfaces 28a, 28b may abut outer surface 20 of cell culture insert 12 when affixed to the cell culture insert 12.

In embodiments, frame 14 may be made from a silicon-containing material, such as a polymeric organosilicon. For example, and without limitations, frame 14 may be made from polydimethylsiloxane (PDMS). In other embodiments, frame 14 may be made from any non-toxic material, such as a non-toxic synthetic polymer, a non-toxic naturally occurring polymer, a non-toxic metal, a non-toxic ceramic material, and combinations of two or more thereof. Specific examples of possible materials for making frame 14 include, but are not limited to, polycaprolactone, polyethylene, polypropylene, polystyrene, nylon, polyethylene glycol and its derivatives, fibrin, poly(lactic acid), poly(glycolic acid), poly(lactic acid-co-glycolic acid), polyethylene terephthalate, and combinations of two or more of these.

In embodiments, the solid component 14a may be affixed to the cell culture insert 12 prior to affixing the porous component 14b. As such, the solid component 14a may be closer in space to base 22 at proximal end 16 of cell culture insert 12, and porous component 14b may be closer in space to distal end 18.

In embodiments, frame 14 may be fabricated in any convenient manner. For instance, frame 14 may be produced by additive manufacturing processes, such as by 3-dimensional (3D) printing. An exemplary system and workstation for 3D printing is described in U.S. Pat. No. 9,910,935, issued Mar. 6, 2018, entitled "SYSTEM AND WORKSTATION FOR THE DESIGN, FABRICATION AND ASSEMBLY OF BIO-MATERIAL CONSTRUCTS," the entirety of which is incorporated by reference herein. In embodiments, solid component 14a and porous component 14b may be made from PDMS by 3D printing, cured in an oven at a temperature from 40° C. to 80° C. for a time greater than or equal to 0.5 hour. As the curing temperature is increased, the curing time may be decreased. The cured components 14a, 14b may then be oxidized using a process such as plasma oxidation, for example. In other embodiments, frame 14 may be made by alternative methods, including but not limited to, molding approaches and cutting or punching material in the shape of the frame 14 from a larger sheet of material.

Figure 4:
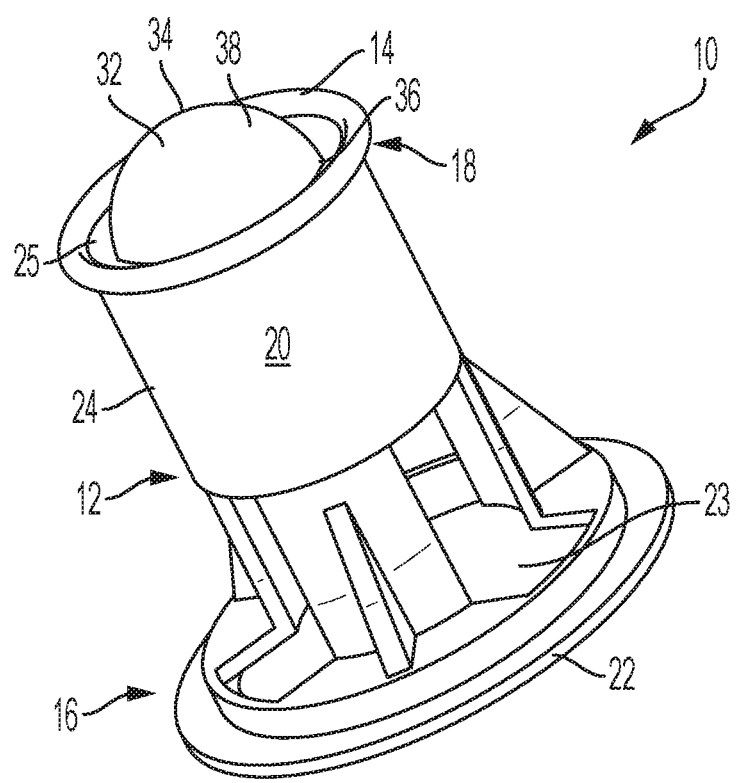
FIG. 4 illustrates a system for fabricating corneas containing a sacrificial dome-shaped member, according to one or more embodiments shown and described herein.

Referring to FIG. 4, system 10 may include a generally dome-shaped member 32. The dome-shaped member 32 includes a crown 34, a dome base 36, and a surface 38 connecting the crown 34 and the dome base 36. The surface 38 projects away from porous membrane 25 such that the crown 34 extends a maximum distance away from the base 22 disposed at the proximal end 16 of the cell culture insert 12. In embodiments, the crown 34 of the dome-shaped member 32 may extend beyond the distal end 18 of the cell culture insert 12 such that a surface for shaping the cornea as it is fabricated extends away from the cell culture insert 12.

Dome-shaped member 32 may be made from a sacrificial material. For example, and without limitation, the sacrificial material may include, but is not limited to, gelatin, poloxamers, alginate, collagen, agarose, sugar glass, fibrin, dissolvable synthetic polymers, and a combination of two or more of these. In embodiments, the sacrificial material may be 3D printable. In other embodiments, the sacrificial material may be able to be deposited by pipetting, physical placement, or any other convenient means of depositing the sacrificial material on the cell culture insert 12.

Figure 5:
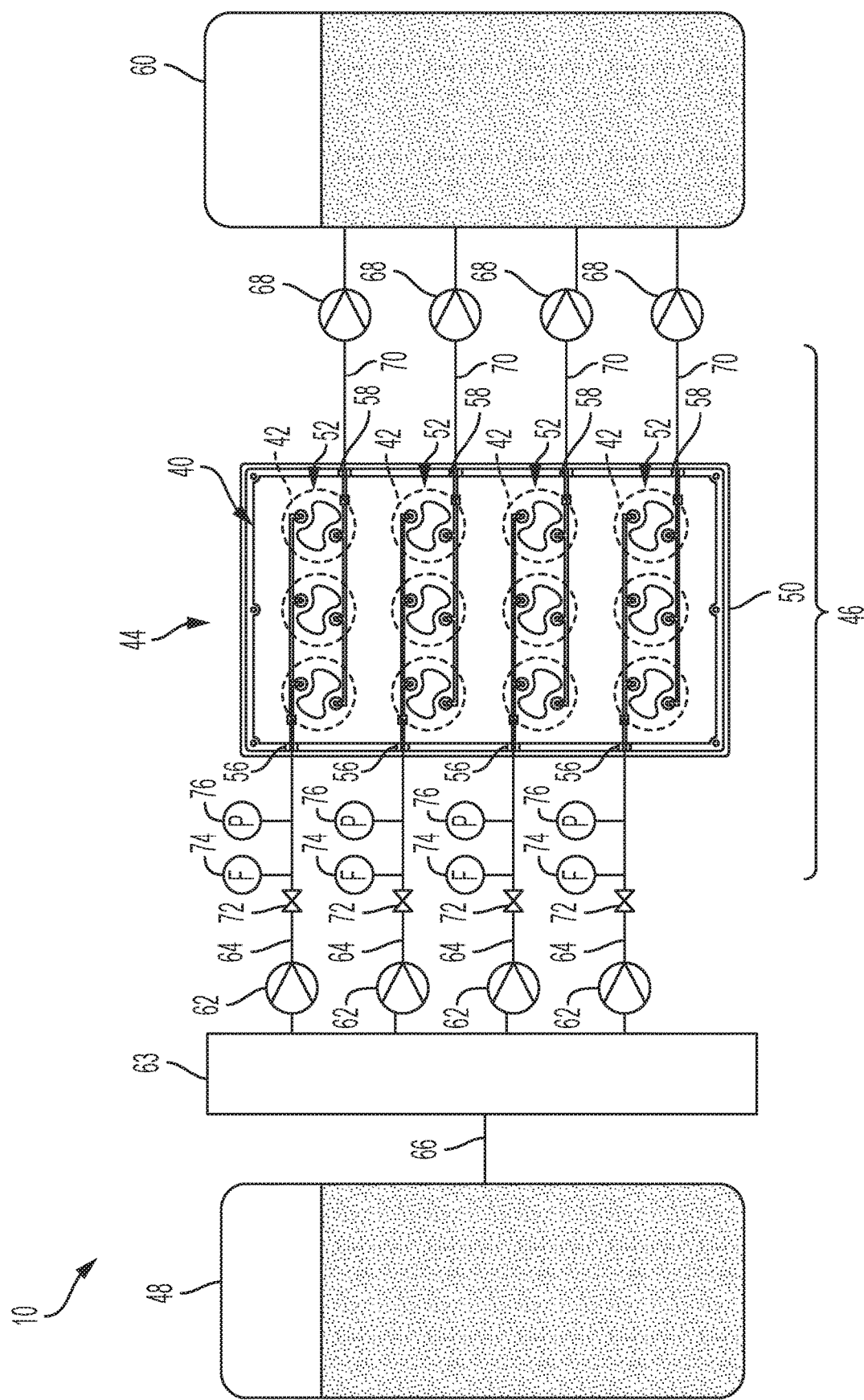
FIG. 5 illustrates a manifold component of a system for fabricating corneas, according to one or more embodiments shown and described herein.

Referring to FIG. 5, system 10 may further include a well-plate manifold 40 for further processing the cornea after formation. An exemplary system that includes a well-plate manifold 40 is described in International Application No. PCT/US2020/021427, entitled "Modular and Expandable Low Flow Pumping Assemblies," filed Mar. 6, 2020, hereby incorporated by reference in its entirety. An exemplary system that includes a well-plate manifold 40 is also described in U.S. patent application Ser. No. 16/811,808, entitled "Modular and Expandable Low Flow Pumping Assemblies," filed Mar. 6, 2020, hereby incorporated by reference in its entirety. In FIG. 5, one or more wells 42 are sized to accommodate at least the distal end 18 of the cell culture insert 12 and the cornea after fabrication. The one or more wells 42 may be arrayed in a well-plate assembly 44. Further, a modular pump assembly 46 may be configured to fluidically couple the well-plate assembly 44 to one or more fluid reservoirs 48.

Well-plate assemblies are described in greater detail in U.S. patent application Ser. No. 16/135,299, entitled "Well-plate and Fluidic Manifold Assemblies and Methods," filed Sep. 19, 2018, hereby incorporated by reference in its entirety. In particular, a well-plate assembly 44 includes a well-plate 50 defining a plurality of well-groups 52. Each well-group 52 may include one or more wells 42. It is noted that well-plates according to the present disclosure may have 6 or more wells, 12 or more wells, 24 or more wells, 48 or more wells, 96 or more wells, etc. The modular pump assembly 46 may be expanded to provide individualized flow control to any number of wells 42 or well-groups 52 within a well-plate 50 such that flow parameters to each well 42 or well-group 52 within a single well-plate 50 may be varied from one another.

A well-plate manifold 40 may be positioned over the well-plate 50 and provide fluid flow paths into and out of each of the wells 42 of the well-plate 50. For example, the well-plate manifold 40 may provide a plurality of fluid inlet paths 56 and a plurality of fluid outlet paths 58. The plurality of fluid inlet paths 56 may provide an inlet into the wells of each well-group 52 and the plurality of fluid outlet paths 58 may provide an outlet for fluid to be removed from each well-group 52 to a receptacle 60 or other location. It is noted that in illustrated embodiment, there are three wells 42 in each well-group 52, however, a greater or fewer number of wells 42 may be in each well-group 52 without departing from the scope of the present disclosure. For example, each individual well 42 may be a well-group 52 and may have a dedicated fluid inlet path 56 and fluid outlet path 58, such that flow to each individual well 42 may be separately controlled.

The inlet pumps 62 fluidically couple each well-group 52 to one or more fluid reservoirs 48. Each inlet pump 62 may be fluidically coupled to the same fluid reservoir 48 as illustrated in FIG. 5. However, it is contemplated that the inlet pumps 62 may be fluidically coupled to different fluid reservoirs 48. Accordingly, different fluid reservoirs 48 may be used for supplying different fluids to different well-groups 52. In some embodiments, each well 42 of the well-plate 50 may be supplied with fluid from a different fluid reservoir 48.

In some embodiments, fluid from the fluid reservoir 48 may first be drawn by one or more inlet pumps 62 into a fluid manifold 63, which may separate the fluid from the fluid reservoir 48 into the fluid inlet lines 64. That is a single first fluid inlet line 66 may fluidically couple the fluid reservoir 48 to the fluid manifold 63, which is then separated to the various fluid inlet lines 64.

Fluid flow through the well-plate manifold 40 may be controlled with the modular pump assembly 46. The modular pump assembly 46 may comprise an array of pumps. The array of pumps may include an array of inlet pumps 62 configured to push fluid through the well-groups 52 of a well-plate 50, an array of outlet pumps 68 configured to pull fluid through the well-groups 52 of the well-plate 50, and/or any combination thereof. For example, in some embodiments the array of pumps includes an array of pump pairs. Each pump pair may include an inlet pump 62 and an outlet pump 68. A fluid inlet line 64 may fluidically couple the inlet pump 62 to a fluid inlet path 56 of the well-plate manifold 40 and a fluid outlet line 70 may fluidically couple the outlet pump 68 to the fluid outlet path 58 of the well-plate manifold 40. The fluid inlet line 64 and fluid outlet line 70 may be any type of tubing, pipes, etc. for containing fluid flow.

The inlet pumps 62 and/or outlet pumps 68 may be any types of pumps including, but not limited to micropumps (e.g., ttpventus BL Series pumps, ttpventus XP Series pumps, ttpventus LT Series pumps, ttpventus HP series pumps, Bartels Mikrotechnik GmbH mp6 micropumps). The inlet pumps 62 and the outlet pumps 68 may be capable of functioning in a small form factor. For example, pumps according to the present disclosure may support low flow rates of 1-2 μl/min. However, greater or smaller flow rates are contemplated and possible. For controlling the flow of fluid through the well-plate assembly 44, each fluid inlet line 64 may include a flow control valve 72, a flow sensor 74, and/or a pressure sensor 76.

In another aspect, in reference to FIGS. 6A-6F, a method of fabricating a cornea includes affixing frame 14 to a cell culture insert 12. The frame 14 and cell culture insert 12 are as described above. Before or after frame 14 is in place, dome-shaped member 32 is affixed to the porous membrane 25 of the cell culture insert 12. A material that includes a matrix-forming compound may then be deposited on the frame 14 and over the dome-shaped member 32 such that the crown 34 and at least a portion of the surface 38 of the dome-shaped member is coated with the material comprising the matrix-forming compound. The dome-shaped member 32 may then be removed, leaving a fabricated cornea 78 attached to the frame 14.

Figure 6A:
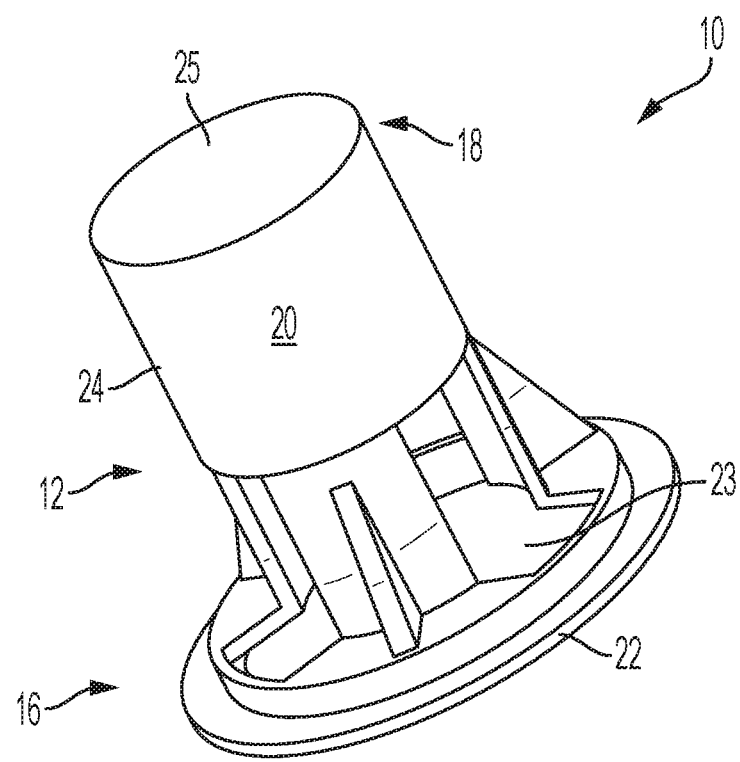
FIG. 6A illustrates a blank cell culture insert component of a system for fabricating corneas, according to one or more embodiments shown and described herein.
Figure 6B:
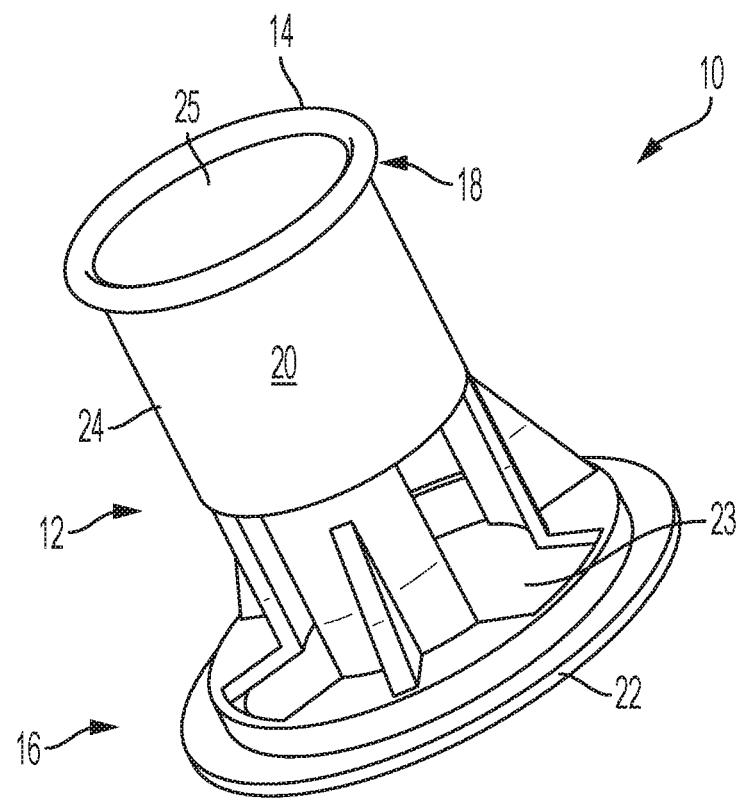
FIG. 6B illustrates the blank cell culture insert of FIG. 6A on which a frame composed of the solid component of FIG. 2 and porous component of FIG. 3 has been affixed, according to one or more embodiments shown and described herein.

Referring to FIGS. 6A and 6B, frame 14 may be affixed to a blank cell culture insert 12 near the distal end 18 and encircling porous membrane 25. As described above, frame 14 may be composed of solid component 14a and porous component 14b. In such embodiments, the solid component 14a is typically affixed to the cell culture insert 12 first, followed by the porous component 14b. When the material comprising a matrix-forming compound is first added to the frame 14 and cell culture insert 12, the material is added in the liquid phase, passing through the porous component 14b and pooling on the solid component 14a.

Figure 6C:
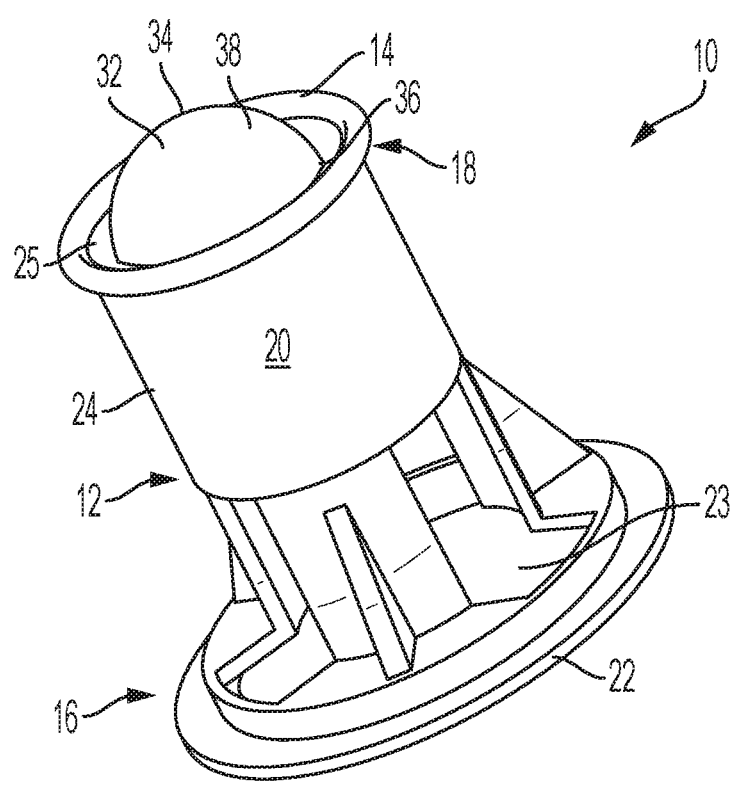
FIG. 6C illustrates a system for fabricating corneas containing a sacrificial dome-shaped member affixed to the system shown in FIG. 6B, according to one or more embodiments shown and described herein.
Figure 6D:
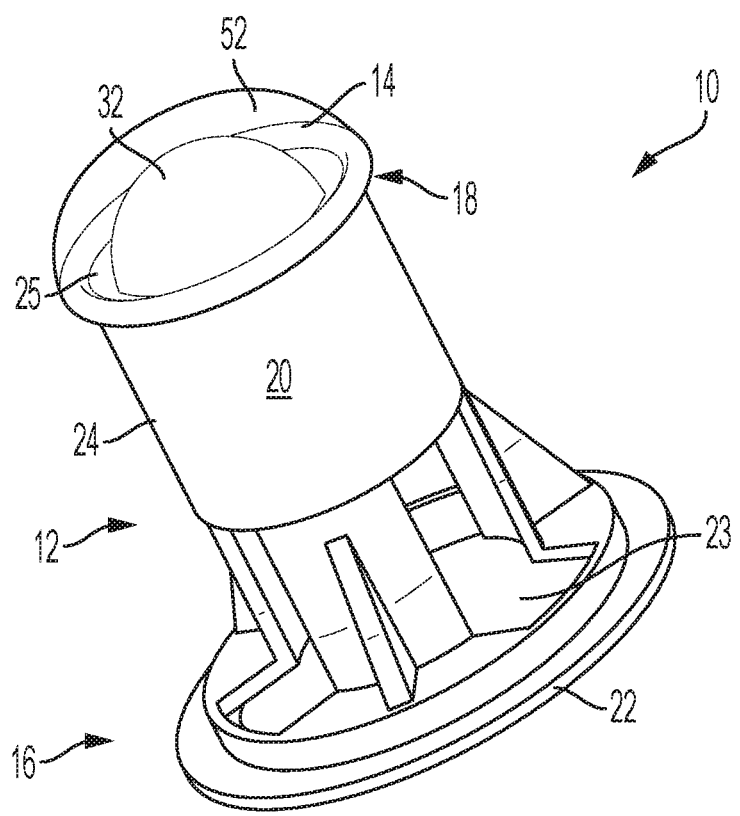
FIG. 6D illustrates a system for fabricating corneas containing a sacrificial dome-shaped member and a cornea affixed to the system shown in FIG. 6C, according to one or more embodiments shown and described herein.

Referring to FIG. 6C, dome-shaped member 32 may be directly deposited on the porous membrane 25 of cell culture insert 12. This dome-shaped member 32 should be constructed from an easily removed material, because it will be sacrificed at a later stage of the method. For instance, the dome-shaped member 32 may be 3D printed from collagen to precisely match the specific anatomy of desired final cornea. Referring to FIG. 6D, the dome-shaped member 32 is at least partially coated with the material comprising the matrix-forming compound to give a fabricated cornea 78.

In embodiments, the matrix-forming compound includes, but is not limited to, functionalized polyethylene glycol hydrogels, chitosan, silk, corneal extracellular matrix, elastin, fibrin, hyaluronan, collagen 2, collagen 3, collagen 4, collagen 10, mouse sarcoma cell extracellular matrix, laminin, polycaprolactone, polyethylene, polypropylene, polystyrene, nylon, polyethylene glycol and its derivatives, fibrin, poly(lactic acid), poly(glycolic acid), poly(lactic acid-co-glycolic acid), polyethylene terephthalate, and combinations of two or more of these.

In embodiments, the matrix-forming compound may be formulated in any convenient concentration. For instance, the matrix-forming compound may be formulated in a solution at a concentration from 1 mg/ml to 30 mg/ml, from 2 mg/ml to 29 mg/ml, from 3 mg/ml to 28 mg/ml, from 4 mg/ml to 27 mg/ml, from 5 mg/ml to 26 mg/ml, from 6 mg/ml to 25 mg/ml, from 7 mg/ml to 24 mg/ml, from 8 mg/ml to 23 mg/ml, from 9 mg/ml to 22 mg/ml, from 10 mg/ml to 21 mg/ml, from 11 mg/ml to 20 mg/ml, from 12 mg/ml to 19 mg/ml, from 13 mg/ml to 18 mg/ml, from 14 mg/ml to 17 mg/ml, or even from 15 mg/ml to 16 mg/ml.

In embodiments, the material comprising the matrix-forming compound may also include cellular material. For example, the material may include collagen and cellular material. In embodiments, the cellular material includes corneal fibroblasts (also known as keratocytes) and/or corneal endothelium cells and/or corneal epithelium cells. In embodiments, the keratocytes and/or endothelium cells and/or epithelium cells may be pre-mixed with the material comprising the matrix-forming compound. In other embodiments, the keratocytes and/or endothelium and/or epithelium cells may be applied to the surface of the cornea after fabrication. Possible sources of the cellular material include, but are not limited to, stem cells.

Figure 6E:
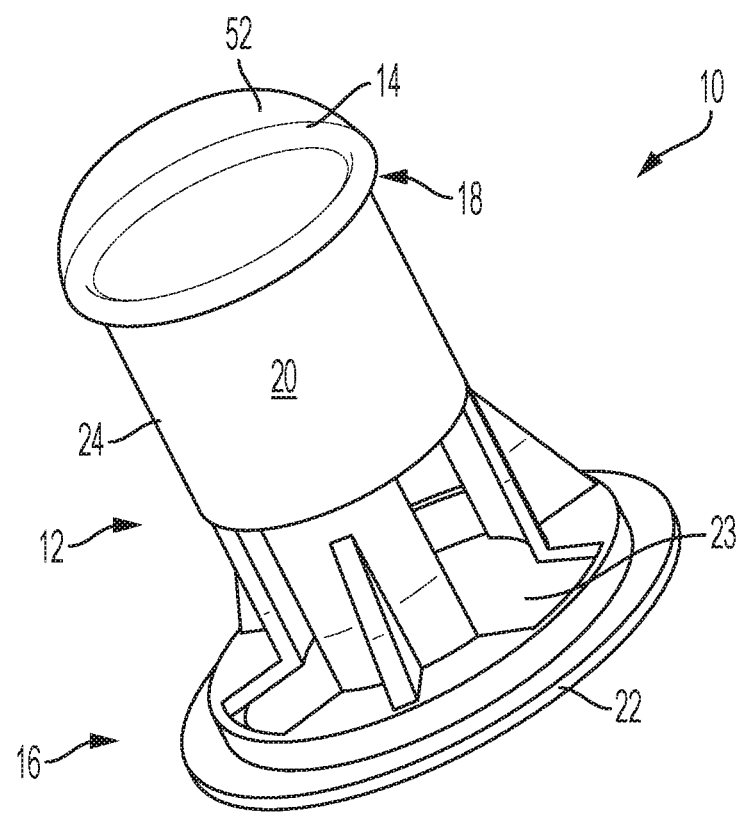
FIG. 6E illustrates a system for fabricating corneas containing a cornea affixed to the system shown in FIG. 6D with the sacrificial dome-shaped member removed, according to one or more embodiments shown and described herein.

Once the fabricated cornea 78 is formed over the dome-shaped member 32, the dome-shaped member 32 is removed from the cell culture insert 12, leaving the fabricated cornea 78 affixed to cell culture insert 12, as shown in FIG. 6E. To accomplish removal of the dome-shaped member 32, the cell culture insert 12 and associated fabricated cornea 78 and dome-shaped member 32 may be submerged in an aqueous solution capable of acting as a dissolution medium. Exemplary dissolution media include, but are not limited to, phosphate buffered saline (PBS).

Figure 6F:
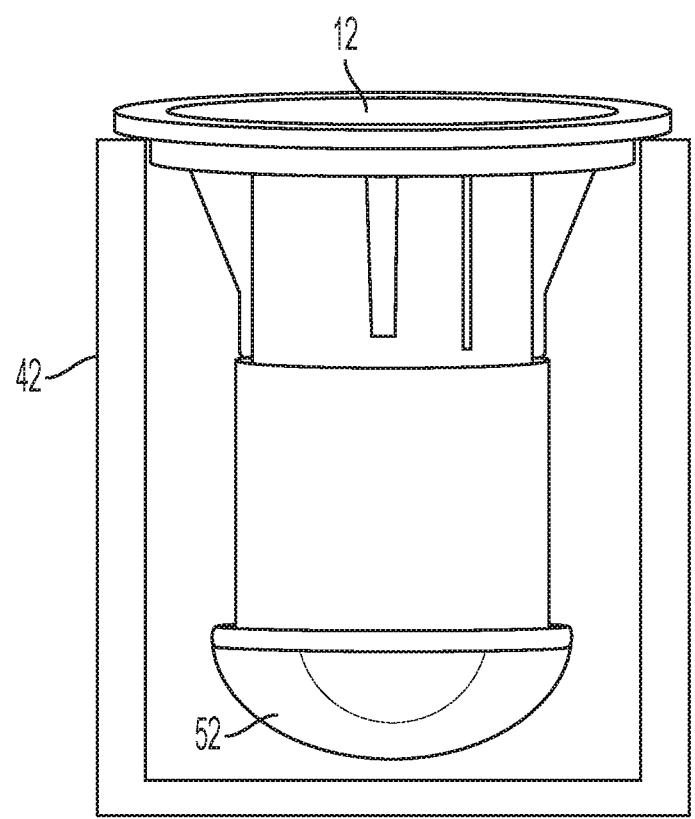
FIG. 6F illustrates the system shown in FIG. 6E housed in a well of a manifold, according to one or more embodiments shown and described herein.

Once formed, the fabricated cornea 78 undergoes a perfusion process in a well 42, as shown in FIG. 6F. Perfusion is used to slowly introduce an amount of fluid flow through the fabricated cornea 78. Without intending to be bound by any particular theory, it is believed that the fluid flow creates small forces on cells, and that these small forces affect the performance of the fabricated cornea 78. Additionally, it is believed that the perfusion aids in the transport of oxygen and nutrients into the fabricated cornea 78 and waste products out of the fabricated cornea 78. When cellular material is not included in the fabricated cornea 78, the perfusion is expected to facilitate matrix component alignment via interstitial convective flows and circumferential stretching secondary to fluid pushing the cornea outward. The cell culture insert 12 allows the perfusion fluid to be added through the aperture 23 at the base 22 of cell culture insert 12 into the hollow interior of the cylinder 24. The perfusion fluid can then flow through porous membrane 25 and through the fabricated cornea 78. In this manner, the physical integrity of the fabricated cornea 78 may be protected from the full pressure of the injection of perfusion fluid due to the presence of the porous membrane 25 between the inlet port 44 (see FIG. 5) and the fabricated cornea 78. Perfusion time may vary and may be at least about 8 hours, although may be less. In aspects, perfusion time may be from 8 hours to 1 month, from 1 day to 2 months, from 1 week to 7 weeks, from 2 weeks to 6 weeks, or even from 3 weeks to 5 weeks. It should be understood that the perfusion time may be from any of the lower limits of such perfusion time described herein to any of the upper limits of such perfusion time described herein.

After perfusion, the fabricated cornea 78 may be removed from the cell culture insert 12 by severing contact between the fabricated cornea 78 and the frame 14.

In another aspect, a fabricated cornea scaffold includes a non-naturally occurring domed structure having a convex surface and a concave surface. In embodiments, the non-naturally occurring domed structure includes a matrix comprising at least one of the matrix-forming compounds described above. In embodiments, the matrix may comprise collagen. In embodiments, the fabricated cornea may be a fabricated living cornea including the fabricated cornea scaffold, a plurality of corneal keratocytes dispersed within the matrix, a plurality of corneal endothelium cells disposed on the concave surface, and a plurality of corneal epithelium cells disposed on the convex surface.

In embodiments, at least a portion of the keratocytes may be autologous, i.e., cultured from cells of the intended recipient of the fabricated cornea, the remaining keratocytes being allogeneic, i.e., cultured from cells of a donor that is not the intended recipient. In other embodiments, all of the keratocytes are autologous. In other embodiments, all of the keratocytes are allogeneic.

In embodiments, at least a portion of the endothelium cells may be autologous, i.e., cultured from cells of the intended recipient of the fabricated cornea, the remaining endothelium cells being allogeneic, i.e., cultured from cells of a donor that is not the intended recipient. In other embodiments, all of the endothelium cells are autologous. In other embodiments, all of the endothelium cells are allogeneic. In embodiments, endothelium cells may be derived from stem cells.

In embodiments, at least a portion of the epithelium cells may be autologous, the remaining epithelium cells being allogeneic. In other embodiments, all of the epithelium cells are autologous. In other embodiments, all the epithelium cells are allogeneic. In embodiments, epithelium cells may be derived from stem cells.

The systems and methods described herein enable certain operation benefits. First, the toroidal frame sets the outer dimensions of the fabricated cornea, an important dimension for proper fit to the recipient of the cornea, while allowing mobility of the remainder of the cornea during the perfusion process. Thus, the cornea is able to adopt an optimal geometry during fabrication. Second, the sacrificial dome-shaped member allows proper shaping of the material comprising the matrix-forming compound and then can be removed easily for subsequent processing of the cornea, e.g., no mold structure is present during the perfusion process to impede the flow of the perfusion fluid. Third, growing the cornea at the distal end of the cell culture insert allows for easy manipulation of the orientation of the cornea during processing without the need for directly touching the fragile cornea. The proximal end of the cell culture insert provides a convenient location for gripping the fabrication system.

In a first aspect, either alone or in combination with any other aspect, a method for fabricating a cornea includes affixing a frame to at least one cell culture insert comprising a generally cylindrical structure having a proximal end and a distal end, a base disposed at the proximal end, and a porous membrane disposed between the proximal end and the distal end; affixing a dome-shaped member to the porous membrane within the frame, the dome-shaped member comprising a crown, a dome base, and a surface connecting the crown and the dome base; depositing a material comprising a matrix-forming compound on the frame such that the crown and at least a portion of the surface of the dome-shaped member is coated with the material comprising the matrix-forming compound; and removing the dome-shaped member to produce a fabricated cornea attached to the frame.

In a second aspect, either alone or in combination with any other aspect, the frame comprises a toroidal shape having an inner surface that abuts an outer surface of the at least one cell culture insert.

In a third aspect, either alone or in combination with any other aspect, the frame comprises a solid component and a porous component disposed adjacent the solid component.

In a fourth aspect, either alone or in combination with any other aspect, the depositing comprises applying the material comprising the matrix-forming compound to the porous component and allowing said material to pass through the porous component and accumulate on the solid component.

In a fifth aspect, either alone or in combination with any other aspect, the affixing the dome-shaped member to the porous membrane comprises 3D printing a sacrificial material onto the porous membrane.

In a sixth aspect, either alone or in combination with any other aspect, the depositing comprises 3D printing a collagen matrix comprising corneal keratocytes on the frame.

In a seventh aspect, either alone or in combination with any other aspect, the removing the dome-shaped member comprises contacting the dome-shaped member with a dissolution medium.

In an eighth aspect, either alone or in combination with any other aspect, the method further comprises flowing a culture medium through the material comprising the matrix-forming compound for from 8 hours to 1 month.

In a ninth aspect, either alone or in combination with any other aspect, the method further comprises separating the fabricated cornea from the frame.

In a tenth aspect, either alone or in combination with any other aspect, a system for fabricating a cornea includes at least one cell culture insert, the cell culture insert comprising a generally cylindrical structure having a proximal end and a distal end, a base disposed at the proximal end, and a porous membrane disposed between the proximal end and the distal end; and a frame disposed on the at least one cell culture insert.

In a eleventh aspect, either alone or in combination with any other aspect, the system further comprises a generally dome-shaped member disposed on the porous membrane, wherein the dome-shaped member comprises a crown, a dome base, and a surface connecting the crown and the dome base; and the surface projects from the porous membrane such that the crown extends away from the base disposed at the proximal end of the at least one cell culture insert and beyond the distal end of the at least one cell culture insert.

In a twelfth aspect, either alone or in combination with any other aspect, the dome-shaped member comprises a sacrificial material.

In a thirteenth aspect, either alone or in combination with any other aspect, the sacrificial material comprises gelatin.

In a fourteenth aspect, either alone or in combination with any other aspect, the gelatin is 3D-printable gelatin.

In a fifteenth aspect, either alone or in combination with any other aspect, the system further comprises an assembly for holding the at least one cell culture insert, the assembly comprising a well-plate manifold and a well-plate assembly comprising a plurality wells sized to accommodate the at least one cell culture insert.

In a sixteenth aspect, either alone or in combination with any other aspect, the assembly comprises at least one fluid inlet line for introducing a fluid to the base disposed at the proximal end of the at least one cell culture insert and at least one outlet line for removing the fluid from the plurality of wells.

In a seventeenth aspect, either alone or in combination with any other aspect, the system further comprises at least one pump fluidically connected to the at least one inlet line and at least one pump fluidically connected to the at least one outlet line.

In an eighteenth aspect, either alone or in combination with any other aspect, a fabricated cornea scaffold includes a non-naturally occurring domed structure having a convex surface and a concave surface, the non-naturally occurring domed structure comprising a matrix comprising at least one matrix-forming compound.

In a nineteenth aspect, either alone or in combination with any other aspect, the fabricated cornea scaffold further comprises a plurality of corneal keratocytes dispersed within the matrix, a plurality of corneal endothelium cells disposed on the concave surface, and a plurality of corneal epithelium cells disposed on the convex surface.

In a twentieth aspect, either alone or in combination with any other aspect, at least a portion of at least one of the plurality of corneal keratocytes, the plurality of corneal endothelium cells, and the plurality of corneal epithelium cells are autologous.

In a twenty-first aspect, either alone or in combination with any other aspect, at least a portion of at least one of the plurality of corneal keratocytes, the plurality of endothelium cells, and the plurality of corneal epithelium cells are allogeneic.

EXAMPLES

Fabrication of the frame: SE 1700 polymer base (20 g) was combined with curing agent (2 g) and mixed. Separately, SYLGARD™ 184 polymer base (10 g) was combined with curing agent (1 g) and mixed. The SYLGARD™ 184 mixture was added to the SE 1700 mixture in a 1:4 w/w ratio and mixed thoroughly, providing a 3D printable PDMS composition. This PDMS composition was then printed into the desired shape, cured in an oven at 60° C. for at least one hour, and then plasma oxidized for one minute. The resulting frame was placed on a TRANSWELL® insert.

Fabrication of a Gelatin Dome: A 6% gelatin solution was prepared and partially gelled in a 4° C. chiller for approximately 30 minutes. The partially gelled gelatin was allowed to equilibrate at 24° C. for 1 hour. This gelatin solution was used to directly print the dome on the porous membrane of the TRANSWELL® insert to which the frame was previously added.

Fabrication of the Cornea Scaffold: A 6 mg/ml collagen solution was prepared and combined with Dulbecco's modified eagle medium (DMEM) and UltraPure water. Sodium hydroxide solution may be added to bring the pH of the solution to 7.4. This collagen solution was then pipetted onto the previously fabricated frame and gelatin dome.

Removal of the Gelatin Dome and Culture: The TRANSWELL® insert with the cornea and dome was placed in an incubator for 30 minutes to allow the collagen to gel, then submerged in PBS dissolution medium. While submerged, the TRANSWELL® insert was returned to the incubator, and the gelatin was allowed to dissolve overnight. The cornea was then cultured by flowing a culture medium through the TRANSWELL® insert, across the porous membrane and across the cornea.

The fabricated cornea was then severed from the TRANSWELL® insert.

For the purposes of describing and defining the present disclosure, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed disclosure or to imply that certain features are critical, essential, or even important to the structure or function of the claimed disclosure. Rather, these terms are merely intended to identify particular aspects of an embodiment of the present disclosure or to emphasize alternative or additional features that may or may not be utilized in a particular embodiment of the present disclosure.

For the purposes of describing and defining the present disclosure it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for fabricating a cornea, comprising:
    at least one cell culture insert, the cell culture insert comprising a generally cylindrical structure having a proximal end and a distal end, a base disposed at the proximal end, and a porous membrane disposed between the proximal end and the distal end;
    a frame disposed on the at least one cell culture insert;
    a generally dome-shaped member disposed on the porous membrane, wherein:
        the dome-shaped member comprises a crown, a dome base, and a surface connecting the crown and the dome base;
        the surface projects from the porous membrane such that the crown extends away from the base disposed at the proximal end of the at least one cell culture insert and beyond the distal end of the at least one cell culture insert; and
        the dome-shaped member comprises a sacrificial material; and
    a fabricated cornea, wherein:
        the fabricated cornea comprises a matrix-forming compound deposited on the frame and the dome-shaped member such that the crown and at least a portion of the surface of the dome-shaped member are coated with the matrix-forming compound.

2. The system of claim 1, wherein the sacrificial material comprises gelatin.

3. The system of claim 2, wherein the gelatin is 3D-printable gelatin.

4. The system of claim 1, further comprising an assembly for holding the at least one cell culture insert, the assembly comprising a well-plate manifold and a well-plate assembly comprising a plurality of wells sized to accommodate the at least one cell culture insert.

5. The system of claim 4, wherein the assembly comprises at least one fluid inlet line for introducing a fluid to the base disposed at the proximal end of the at least one cell culture insert and at least one outlet line for removing the fluid from the plurality of wells.

6. The system of claim 5, further comprising at least one pump fluidically connected to the at least one inlet line and at least one pump fluidically connected to the at least one outlet line.

7. The system of claim 1, wherein the matrix-forming compound is selected from the group consisting of: functionalized polyethylene glycol hydrogels, chitosan, silk, corneal extracellular matrix, elastin, fibrin, hyaluronan, collagen 2, collagen 3, collagen 4, collagen 10, mouse sarcoma cell extracellular matrix, laminin, polycaprolactone, polyethylene, polypropylene, polystyrene, nylon, polyethylene glycol and its derivatives, fibrin, poly(lactic acid), poly(glycolic acid), poly(lactic acid-co-glycolic acid), polyethylene terephthalate, and combinations thereof.

8. The system of claim 1, wherein the matrix-forming compound further comprises cellular material.

* * * * *